United States Patent
Kline et al.

(10) Patent No.: US 8,636,369 B2
(45) Date of Patent: Jan. 28, 2014

(54) PREVENTION AND REMEDIATION OF DAMAGE TO OPTICAL SURFACES

(75) Inventors: Eric V Kline, Rochester, MN (US); Yves C Martin, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 455 days.

(21) Appl. No.: 12/907,904

(22) Filed: Oct. 19, 2010

(65) Prior Publication Data
US 2012/0092765 A1 Apr. 19, 2012

(51) Int. Cl.
*B60R 1/06* (2006.01)

(52) U.S. Cl.
USPC .......................................... 359/507

(58) Field of Classification Search
USPC .................................. 359/507–513
See application file for complete search history.

(56) References Cited

U.S. PATENT DOCUMENTS

| | | | |
|---|---|---|---|
| 4,076,373 A * | 2/1978 | Moretti | 359/507 |
| 4,138,746 A | 2/1979 | Bergmann | |
| 4,428,081 A | 1/1984 | Smith | |
| 5,002,326 A | 3/1991 | Westfield et al. | |
| H1023 H | 3/1992 | Wiseman, Sr. | |
| 5,592,698 A | 1/1997 | Woods | |
| 5,685,022 A | 11/1997 | Essman et al. | |
| 6,415,452 B1 | 7/2002 | Watanabe et al. | |
| 7,540,039 B2 | 6/2009 | Reaux | |
| 7,629,052 B2 | 12/2009 | Brumwell | |
| 2007/0024982 A1 | 2/2007 | Stickel et al. | |
| 2008/0198456 A1* | 8/2008 | Sharp | 359/499 |
| 2008/0297745 A1 | 12/2008 | Weissenrieder et al. | |
| 2009/0242526 A1 | 10/2009 | Baldwin | |
| 2009/0314429 A1 | 12/2009 | Hoya et al. | |

FOREIGN PATENT DOCUMENTS

| | | |
|---|---|---|
| GB | 2367119 | 3/2002 |
| GB | 2452899 | 3/2009 |
| JP | 3015951 | 1/1991 |
| JP | 6347611 | 12/1994 |

OTHER PUBLICATIONS

IBM TDB, Protective Shield for Laser Lens, Mar. 1, 1971, 3 pages.
EM Electronics, Placement of Lens Protective Film Onto Mobile Phone Lens, 2010, 2 pages, www.mmm.com/electronics.
Matin LCD Monitor Protective Film for Nikon D90, 2010, 1 page.

* cited by examiner

Primary Examiner — James Jones
(74) Attorney, Agent, or Firm — Steven L. Bennett

(57) ABSTRACT

A polylaminate film system for protecting optical surfaces, such as a lens, has plural polymer thin films arranged in a polylaminate stack, with each thin film coupled to adjacent films via solvent welding. The film system is adhered to the optical surface to be protected and, as each film in the stack becomes damaged or dirty, it may be sequentially removed to present a clean film surface. The transparent film may be composed of the same material as the optical surface to minimize distortion and loss of optical transmission when radiation passes through the combined film and lens.

17 Claims, 3 Drawing Sheets

PREVENTION AND REMEDIATION OF DAMAGE TO OPTICAL SURFACES

BACKGROUND

The present invention relates to optical surfaces, and more specifically, to the prevention of damage to optical surfaces and/or the mitigation of existing damage to optical surfaces.

Many optical systems, particularly when installed out-of-doors or in some other hazardous environment, are exposed to potential damage. Such damage may occur due to exposure to ultraviolet light (UV), excess humidity, particulates, and so on. In many cases, replacement of the damaged optics may not be practical, either due to the inaccessibility of the optical system, or the expense of such a procedure. It may therefore be desirable to implement strategies for protecting such exposed optical systems, and/or to remediate such damage when it occurs.

BRIEF SUMMARY

According to one embodiment, the present invention includes a film system corresponding to a plurality of polymer thin films arranged in a polylaminate stack, where each thin film is coupled to each adjacent film via solvent welding.

In another embodiment, the present invention includes a method of assembling a polylaminate film system, the method including exposing plural polymer thin films to a solvent, arranging the thin films in a pile, compressing the pile, and curing the thin films such that each thin film is separably decouplable from the adjacent thin films.

In yet another embodiment, the present invention includes a polylaminate film system where the film system is prepared by a process that includes arranging a plurality of polymer thin films in a stack, and coupling each thin film to the adjacent films using solvent welding.

In yet another embodiment, the present invention includes an optics system, where the optical system includes an optical component having an optical surface, and a polylaminate stack of plural polymer thin films adhered to the optical surface, where each thin film in the polylaminate stack is coupled to the adjacent films in the stack via solvent welding, and is sequentially removable from the polylaminate stack.

Yet another embodiment of the present invention includes a method of reconditioning a plastic lens that is exhibiting environmental damage, the method including selecting an organic solvent capable of softening a surface of the plastic lens, applying the selected organic solvent to the plastic lens surface so that the plastic lens softens and thereby repairs at least some of the environmental damage to the lens surface, and curing the plastic lens.

Yet another embodiment of the present invention includes a method of protecting an optical lens surface from environmental damage, the method including disposing a transparent film across the surface of the optical lens, where the transparent film is composed of the same material as the optical lens and so thereby minimizes distortion and loss of optical transmission when radiation passes through the combined film and lens, providing a supply magazine to supply the transparent film across the optical lens surface, providing a take-up magazine to recover the transparent film after it has passed across the optical lens surface, and advancing the transparent film from the supply magazine to the take-up magazine in order to provide unused transparent film across the surface of the optical lens.

Yet another embodiment of the present invention includes an apparatus for protecting a surface of an optical lens from environmental damage, where the apparatus includes a chassis that is coupled with the optical lens, a supply magazine that is disposed at a first side of the optical lens and attached to the chassis, the supply magazine including a supply roller of a transparent film, a take-up magazine disposed at a second side of the optical lens and attached to the chassis, where the take-up magazine includes a take-up roller for the transparent film, and an advance mechanism that can advance the transparent film from the supply roller to the take-up roller so that unused transparent film may be applied across the surface of the optical lens when the advance mechanism is activated. In this embodiment, the transparent film is composed of the same material as the optical lens to minimize distortion and loss of optical transmission when radiation passes through the combined film and lens.

DETAILED DESCRIPTION

Figure 1:
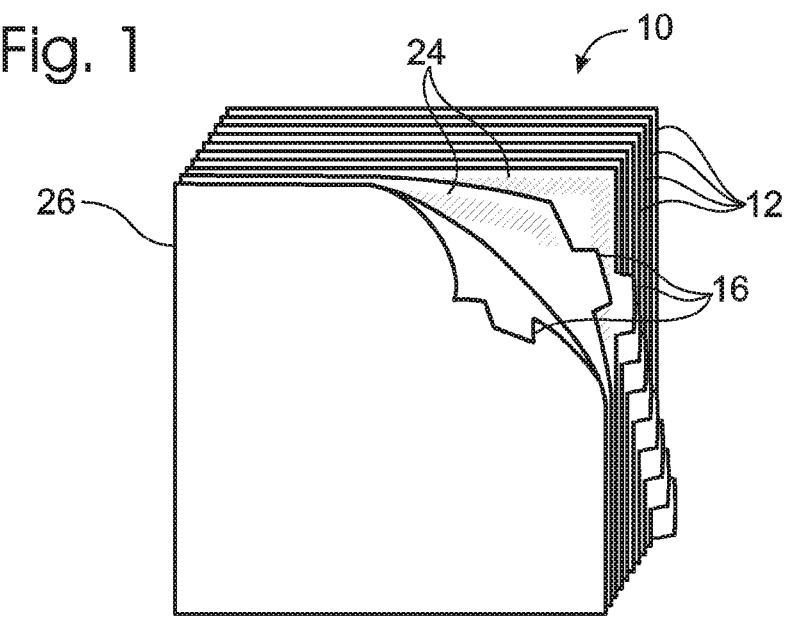
FIG. 1 schematically depicts a polylaminate film stack according to one embodiment of the present invention.

FIG. 1 depicts a film stack 10 according to one embodiment of the invention. Film stack 10 may include a plurality of thin films 12 arranged in a polylaminate fashion. By polylaminate is meant that the thin films, or laminae, form multiple consecutive layers in the film stack. Each of the thin films making up film stack 10 is physically coupled to the adjacent films, but the films may nevertheless be sequentially removed.

The thin films that make up the film stack may be plastic. As used herein, plastic is meant to include any of a large variety of organic polymers that may be formed into pliable sheets or thin films. More particularly, the thin films may be composed of acrylic, polypropylene, polyethylene, polycarbonate, polypropylene, PVC, polyurethane, or polyester, among others. In one embodiment of the of the invention, the thin films are composed of acrylic plastic.

Referring to FIG. 1, film stack 10 is depicted schematically, and so the relative thicknesses of films 12 and the interfilm spacing shown in FIG. 1 are not intended to reflect the actual dimensions of a representative polylaminate film stack. For example, each thin film 12 may have a thickness of between about 0.005 mm to about 30 mm. In another example, each thin film may have a thickness of between about 0.2 mm to about 25 mm. In yet another example, each thin film may have a thickness of between about 2 mm to about 10 mm.

The physical coupling that exists between the thin plastic films is typically strong enough to prevent the film stack from any unintentional separation of thin films from the bulk of the stack, while still permitting an individual thin film to be removed from the film stack without excessive effort. This type of separable, or reversible, coupling may be accomplished by solvent welding, also known as solvent bonding.

In solvent welding, a solvent is applied to a polymer composition, with the result that the polymer composition swells, becoming temporarily and partially dissolved. Under these conditions, the individual polymer chains of the composition become relatively mobile, and when placed in contact with a second polymer composition that has similarly been treated with solvent and is similarly swollen, the polymer chains of the two compositions can become physically entangled. Once sufficiently intermingled, the resulting bond, or weld, becomes cured upon removal of the applied solvent by diffusion and/or evaporation, a process that may be speeded by the application of heat. Upon curing, the individual polymer chains in the compositions lose their mobility, and the two polymer compositions become physically coupled.

Figure 2:
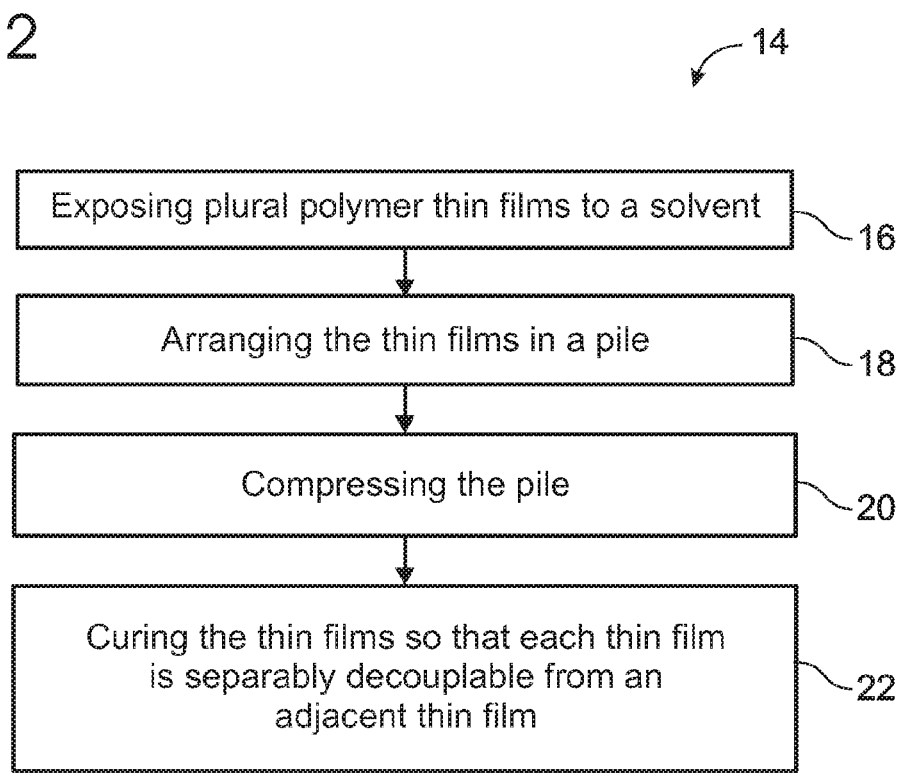
FIG. 2 depicts a flowchart illustrating a method of assembling a polylaminate film system, according to yet another embodiment of the present invention.

In particular, polylaminate film stack 10 may be prepared according to the method outlined in flowchart 14 of FIG. 2, where the method includes exposing plural polymer thin films to a solvent, at 16; arranging the thin films in a pile, at 18; compressing the pile, at 20; and curing the thin films so that each thin film is separably decouplable from an adjacent thin film, at 22.

Any solvent that is compatible with the plastic used to prepare the thin films of the film stack is a suitable solvent for the purposes of preparing a polylaminate film stack. By compatible is meant that the solvent is capable of swelling the plastic, and may facilitate solvent welding, without the degradation or dissolution of the polymer thin film. The solvent, or mixture of solvents, used may include one or more of ethyl acetate, acetone, diethylene glycol, ethanol, heptane, hexane, toluene, triethyl amine, methylene chloride, tetrahydrofuran, and xylene, among others.

The entire area of thin film 12 may be used for solvent welding, which results in a maximal physical connection between adjacent thin films. However, for some applications, such a secure coupling may require an undesirably strong effort to successfully remove an individual film from stack 10. In addition, the solvent welding process can potentially introduce a degree of optical distortion in the film stack. It is therefore often desirable to couple adjacent thin films by the solvent welding process over less than the total surface of each thin film. In particular, solvent welding may be employed over an area that is less than half the total area of each thin film, resulting in a more easily removable thin film, and less optical distortion created thereby. Preferably, method 14 includes exposing only a portion of the area of each polymer thin film to the selected solvent during solvent welding. More specifically, solvent welding may be employed only along one or more edges of each thin film. In one embodiment, solvent welding is employed along only a single edge of each thin film. In yet another embodiment, solvent welding may be employed at only the corners of each thin film, provided the thin film being coupled has an outline that defines one or more corners. In yet another particular embodiment, as demonstrated by film stack 10 of FIG. 1, adjacent thin films are coupled by solvent welding along only the edges of each thin film, in region 24 along the periphery 26 of the thin films.

Alternatively, or in addition, the strength of the physical coupling between adjacent thin films may be regulated by exposing the polymer thin film to solvent vapor, instead of liquid solvent, resulting in a relatively weaker coupling. Alternatively, or in addition, solvent may be applied to the thin films, which may then be permitted to partially dry before they are assembled into a stack and compressed. In yet another alternative or additional strategy, the thin films may be assembled into a film stack at higher or lower temperatures to regulate the degree of interaction between adjacent films during solvent welding. For example, preparing a film stack at relatively low temperatures (for example, lower than room temperature) may result in a reduction in interfilm bond strength. By utilizing one or more of these tactics when preparing the disclosed film stacks, a greater degree of control of polymer swelling and/or molecular interaction may be achieved, and the strength of the desired interfilm coupling may be more precisely controlled.

In order to facilitate the sequential removal of individual thin films from stack 10, one or more of the thin films may include a tab 28, handle, or other feature configured to assist in selecting and removing an individual thin film. In one embodiment, tab 28 is configured to facilitate removal of an individual thin film manually. In another embodiment, each thin film incorporates one or more features configured to facilitate removal of each individual thin film via mechanical means and/or by an automated process. Such an automated process may be triggered activated at regular intervals, corresponding for example to a defined period of environmental exposure.

The film stacks of the present invention are typically used in conjunction with, or as a component of, an optical system. As used herein, an optical system is any apparatus or installation that includes one or more optical components having an exposed optical surface. An optical component may include any device principally utilized to collect, manipulate, or measure incident radiation. Appropriate examples of optical components include refractometers, interferometers, telescopes, binoculars, periscopes, photodetectors, photomultipliers, solar panels, solar concentrators, cameras, optical sights, rangefinders, and theodolites, among others.

An optical surface corresponds to an exterior, or distal, surface of that portion of an optical component that collects or receives the incident radiation that the optical component subsequently collects, manipulates, or measures. The optical surface may correspond to the external surface of one or more lenses, or the exterior surface of a protective case. In one embodiment, the optical surface is the exterior surface of a lens, particularly a refractive lens. The optical surface may optionally be the external surface of a Fresnel lens.

Where the optical surface of an optical system is exposed to a harmful environment, the optical surface may degrade in performance over time. Typical environmental hazards may include exposure to ultraviolet light, excessive humidity, and/or particulates, among other, that may physically damage and/or degrade the optical characteristics of the optical component. The optical surface may be protected from such hazards by fastening a film stack according to an embodiment of the present invention to the optical surface of the component. Although environmental hazards may damage the outermost surface of the film stack, after sufficient damage is accumulated the outermost thin film may be readily separated from the stack and removed, exposing a new thin film having a new and undamaged outermost surface, thereby restoring the optical properties of the film stack-optical component combination.

The film stack may be fastened to the optical surface by any suitable method. Preferably, the method of attachment of the film stack to the optical surface is selected to preserve the clarity, transmission, and fidelity of the radiation entering the optical component. Where an adhesive is used to adhere the film stack to the optical surface, the adhesive is preferably applied to only the periphery of the optical surface, and more preferably applied beyond the periphery of the optical surface. Alternatively, where the optical surface is composed of a plastic, the film stack may be adhered to the optical surface without the use of adhesives, for example by solvent welding of the film stack directly to the optical surface.

The optical component may be adapted for use with a particular portion of the electromagnetic spectrum. Typically, the optical component is adapted for use with visible radiation, with infrared radiation, or ultraviolet radiation, and is therefore composed of a material having suitable transmissivity and refractive indices for such radiation.

Where the optical surface is the exterior surface of a lens, the lens may be composed of a variety of materials, including glass, quartz, or plastic, among others. The composition of film stack 10 is typically selected so that the radiation transmitted through the film stack exhibits only minimal distortion, or loss of transmission. In particular, the efficacy of the optical system disclosed herein may be enhanced where the film stack is composed of a plastic that matches the composition of the optical surface being protected, thereby minimizing losses and distortion when radiation passes through the stack and into the optical component.

It should be appreciated that the optical surface may be a substantially flat surface. However, it may alternatively exhibit some curvature, either concave or convex, or other distinct surface geometry. Where the optical surface is not flat, the film stack intended for application to that particular surface may be prepared so that it possesses a surface geometry matching that of the optical surface it will be fastened to. In a selected embodiment of the invention, the optical surface is a front surface of a flat Fresnel lens, and the film stack is configured to match that flat surface.

Figure 3:
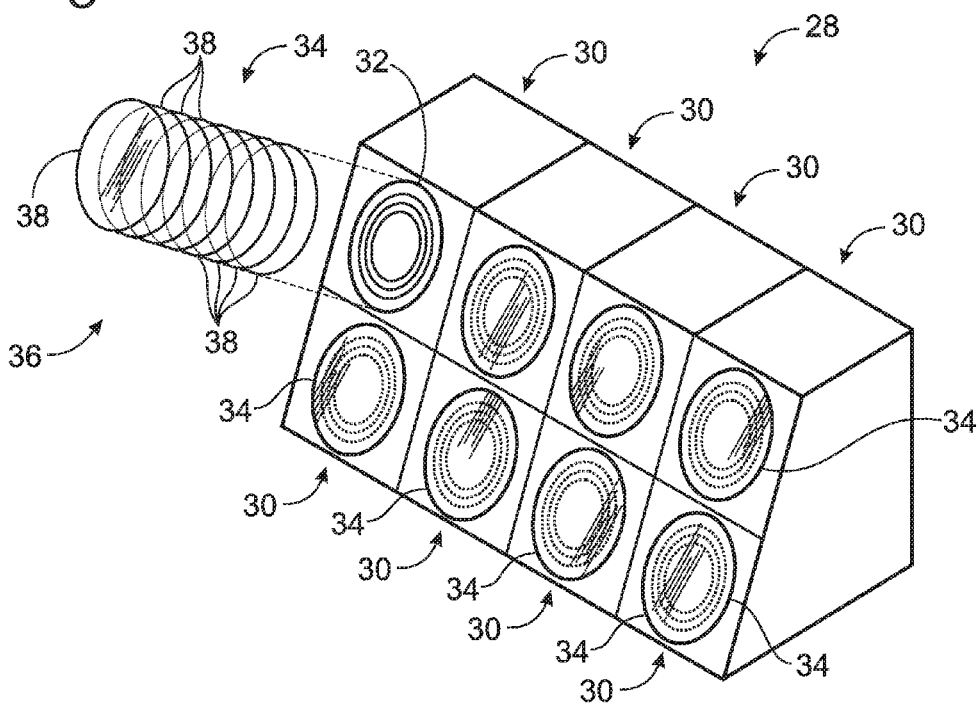
FIG. 3 schematically depicts an optical system according to an embodiment of the present invention.

The thin films that make up film stack 10 may be substantially coincident, that is the periphery of each thin film may be aligned with the periphery of every other thin film. Although film stack 10 of FIG. 1 is depicted as square in shape, and film stack 34 of FIG. 3 is circular, it should be appreciated that a film stack may be prepared having any appropriate or necessary shape. Typically, the shape and/or outline of a particular film stack is selected to correspond to, or complement, the size and shape of the optical surface to be protected by that film stack. In one embodiment, the size and shape of the film stack substantially corresponds to the size and shape of the optical surface to be protected. In another embodiment, the size and shape of the film stack is selected so that the film stack extends beyond the periphery of the optical surface to be protected.

A representative embodiment of an optical system 28 is depicted schematically in FIG. 3. Optical system 28 is composed of multiple individual optical components 30, disposed in an array. The optical components of a given optical system may be arranged in any suitable geometry or number, and are not limited to the size, number, and/or orientation of the representative optical components of FIG. 3. Each optical component 30 includes a circular Fresnel lens 32 having a flat front surface, and each front surface is protected by a film stack 34 adhered to the front surface of the lens. As shown in FIG. 3, film stack 34 is a circular film stack, and in particular as shown in the exploded view at 36, film stack 34 is composed of a plurality of individual thin films 38. Each thin film 38 is coupled to each adjacent film 38 via solvent welding, such that when the outermost thin film becomes damaged, it may be readily removed to expose an undamaged thin film. In this way the operational lifetime of lens 32 may be extended without compromising the efficiency of optical component 30.

Figure 4:
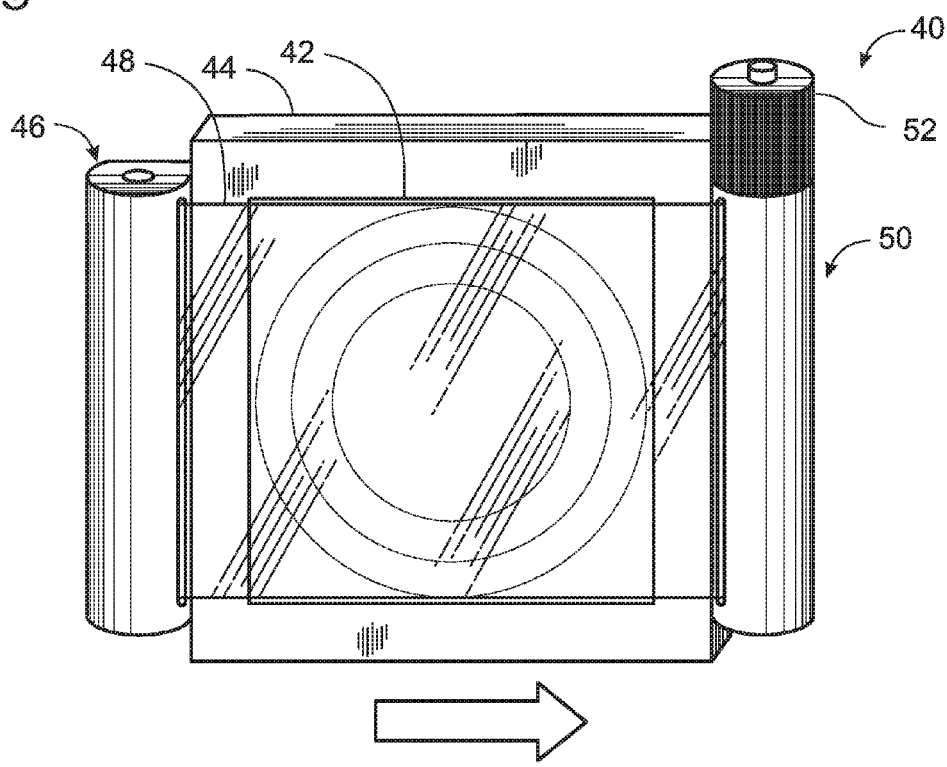
FIG. 4 schematically depicts an apparatus for protecting a surface of an optical lens from environmental damage, according to yet another embodiment of the present invention.

As an alternative to adhering a polylaminate film stack onto an optical surface, the optical surface may be protected by an apparatus incorporating a strip of transparent film. FIG. 4 depicts an exemplary apparatus 40 for protecting a surface of an optical lens 42 from environmental damage, where optical lens 42 is mounted within chassis 44. Apparatus 40 includes a supply magazine 46 attached to chassis 44, where supply magazine 46 includes a supply roller of a transparent film 48 disposed at a first side of optical lens 42. Apparatus 40 further includes a take-up magazine 50, attached to the chassis at a second side of the optical lens, where the take-up magazine includes a take-up roller for transparent film 48. Instead of manually removing individual film sheets, Apparatus 40 incorporates a film advance mechanism 52 for advancing transparent film 48 from supply magazine 46 to take-up magazine 50, so that when the advance mechanism is activated, clean and unused transparent film is supplied across the surface of optical lens 42, in the direction indicated by the arrow. Similar to the film stack discussed previously, the composition of transparent film 48 is typically selected to minimize distortion and loss of optical transmission when radiation passes through the combined film and lens. In one embodiment, the transparent film has the same composition as the optical lens.

Advance mechanism 52 may incorporate any of a variety of suitable mechanisms for advancing transparent film 48, including winding keys, rotary handles, electric motors, and the like. The advance mechanism may be triggered remotely by electrical signal, radio signal, or infrared signal, and/or the advance mechanism may be triggered automatically as part of a scheduled maintenance event. Apparatus 40 may also include a manual advance control, such as a pushbutton 54, that when pressed activates advance mechanism 52 and thereby advances transparent film 48.

Figure 5:
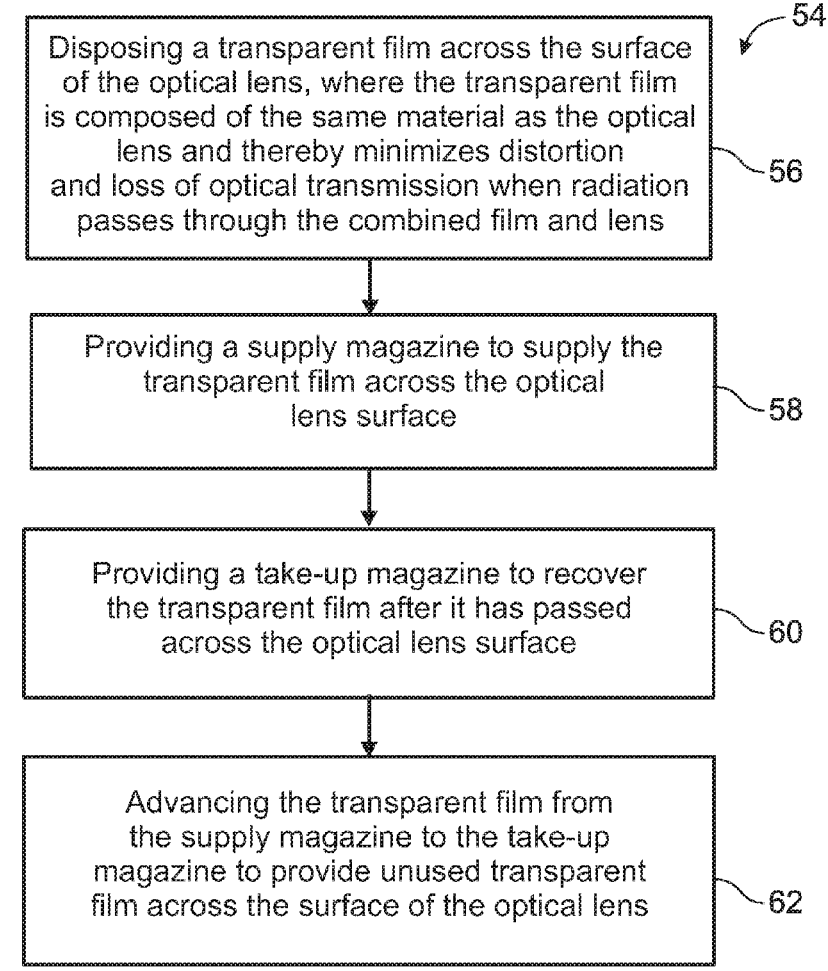
FIG. 5 depicts a flowchart illustrating a method of protecting an optical lens surface from environmental damage, according to yet another embodiment of the present invention.

Apparatus 40 lends itself to a method for protecting an optical lens surface from environmental damage, as set out in flowchart 54 of FIG. 5, which includes disposing a transparent film across the surface of the optical lens, where the transparent film is composed of the same material as the optical lens and thereby minimizes distortion and loss of optical transmission when radiation passes through the combined film and lens, at 56; providing a supply magazine to supply the transparent film across the optical lens surface, at 58; providing a take-up magazine to recover the transparent film after it has passed across the optical lens surface, at 60; and advancing the transparent film from the supply magazine to the take-up magazine to provide unused transparent film across the surface of the optical lens, at 62.

If the exposed surface of a plastic lens already suffers from some type of environmental damage, the application of a transparent film or film stack may not adequately compensate for an existing loss of optical clarity and quality. However, it may be possible to remediate such a damaged plastic lens surface by applying solvent to the damaged lens. As discussed above, upon the application of a suitable organic solvent, the damaged plastic will swell and soften, and the resulting increased molecular mobility may result in the healing of small scratches, defects, and imperfections in the lens surface. Similar, the effects of ultraviolet light damage may be reversed, and the clarity of the lens may be restored.

Figure 6:
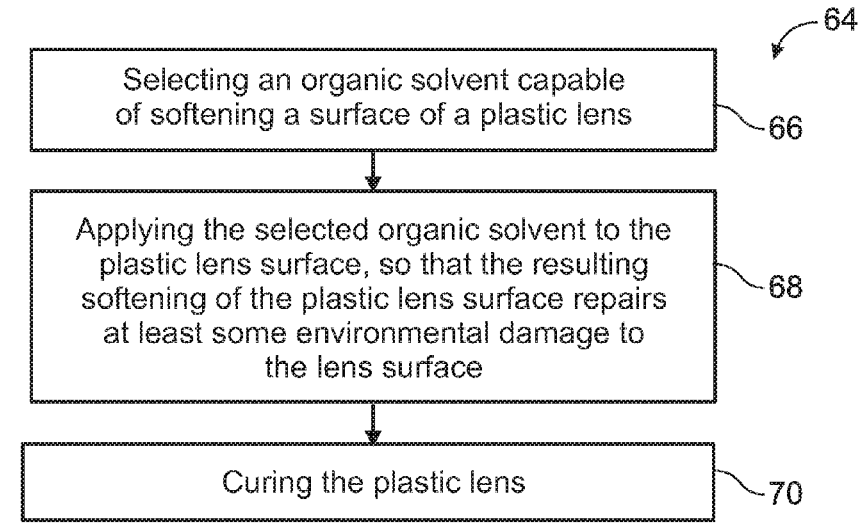
FIG. 6 depicts a flowchart illustrating a method of reconditioning a plastic lens, according to yet another embodiment of the present invention.

As set out in flowchart 64 of FIG. 6, an exemplary method of remediating a plastic lens may include selecting an organic solvent capable of softening the surface of the damaged plastic lens, at 66; applying the selected organic solvent to the plastic lens surface, such that the resulting softening of the plastic lens surface repairs at least some of the environmental damage to the lens surface, at 68; and curing the plastic lens, at 70.

This remediation process may or may not include wiping the lens surface, or a mechanical treatment of the lens surface, in order to remove damaged polymer material, or to artificially smooth the lens surface.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A film system, comprising:
   plural polymer thin films arranged in a polylaminate stack, with each thin film coupled to adjacent films via solvent welding, the stack being constructed so that the thin films are sequentially removable therefrom.

2. The film system of claim 1, wherein each of the thin films has a thickness of about 0.005 mm to about 1 mm.

3. The film system of claim 1, wherein the thin films include acrylic, polycarbonate, polyethylene, polypropylene, PVC, polyurethane, or polyester.

4. The film system of claim 1, wherein each thin film has a total area and plural edges, and each is coupled to an adjacent thin film via solvent welding over an area that is less than half the total area of the film.

5. The film system of claim 4, wherein each thin film is coupled to an adjacent thin film via solvent welding along at least one edge of the film.

6. The film system of claim 1, wherein the stack is configured to minimize distortion and loss of optical transmissions when radiation passes through the stack.

7. The film system of claim 1, further comprising an optical lens, wherein the stack is applied to a surface of the lens.

8. The film system of claim 7, wherein the stack is composed of the same material as the lens, thereby minimizing distortion and loss of optical transmission when radiation passes through the combined stack and lens.

9. The film system of claim 7, wherein the stack substantially covers the surface of the lens.

10. The film system of claim 7, wherein the optical lens is a Fresnel lens.

11. A polylaminate film system, prepared by the process of:
    arranging plural polymer thin films in a stack; and
    coupling each thin film to an adjacent film via solvent welding so that the thin films are sequentially removable from the stack.

12. The polylaminate film system of claim 11, wherein the coupling step includes exposing the thin films to a solvent, placing the exposed thin films in contact with adjacent films, stacking the thin films to create a separable bond between each of them; and curing the stacked thin films.

13. The polylaminate film system of claim 12, wherein the exposing step includes applying a solvent vapor to one or more edges of the thin films.

14. The polylaminate film system of claim 12, wherein exposing step includes exposing the thin films to one or more of ethyl acetate, acetone, diethylene glycol, ethanol, heptane, hexane, toluene, triethyl amine, methylene chloride, tetrahydrofuran, and xylene.

15. The polylaminate film system of claim 12, wherein the arranging step includes arranging plural acrylic thin films in a stack.

16. An optical system, comprising:
    an optical component having an optical surface; and
    a polylaminate stack of plural polymer thin films adhered to the optical surface;
    wherein each thin film is coupled to adjacent films in the polylaminate stack via solvent welding such that each film is sequentially removable from the polylaminate stack.

17. The optical system of claim 16, wherein the optical component is a lens, the polylaminate stack substantially covers a front surface of the lens, and the polylaminate stack is composed of the same material as the lens.

* * * * *